United States Patent [19]

Ayres et al.

US005766623A

[11] Patent Number: 5,766,623
[45] Date of Patent: Jun. 16, 1998

[54] COMPACTABLE SELF-SEALING DRUG DELIVERY AGENTS

[75] Inventors: James W. Ayres, Corvallis, Oreg.; Syed A. Altaf, Mountain View, Calif.; Stephen W. Hoag, Catonsville, Md.

[73] Assignee: State of Oregon Acting By and Through the Oregon State Board of Higher Education on Behalf of Oregon State University, Corvallis, Oreg.

[21] Appl. No.: 621,562

[22] Filed: Mar. 25, 1996

[51] Int. Cl.$^6$ .............................. A61K 9/16; A61K 9/22
[52] U.S. Cl. ............ 424/441; 424/465; 424/468; 424/469; 424/490; 424/497
[58] Field of Search ................... 424/465, 468, 424/441, 458, 490, 497, 493, 469

[56] References Cited

U.S. PATENT DOCUMENTS

| | | | |
|---|---|---|---|
| 4,649,043 | 3/1987 | Urquhart et al. | 424/469 |
| 4,820,521 | 4/1989 | Panoz et al. | 424/458 |
| 4,820,522 | 4/1989 | Radebaugh et al. | 424/468 |
| 4,980,173 | 12/1990 | Halskov | 424/490 |
| 5,096,717 | 3/1992 | Wirth et al. | 424/490 |
| 5,422,122 | 6/1995 | Powell | 424/465 |

OTHER PUBLICATIONS

Development of a New Controlled Release Metoprolol Product, Ragnarsson, et al., *Drug Development and Industrial Pharmacy*, 13 (9–11):1495–1509 (1987).

The Strength and Compaction of Millispheres, Aulton, et al., *Drug Development and Industrial Pharmacy*, 20 (20):3069–3104 (1994).

Coated Pelletized Dosage Form: Effect of Compaction on Drug Release, Béchard, et al., *Drug Development and Industrial Pharmacy*, 18(18):1927–1944 (1992).

Compaction Studies on Pellets: I. Uncoated Pellets. Maganti, et al., *Int. J. Pharm.*, 95:29–42 (1993).

Compaction Studies on Pellets: II. Coated Pellets, Maganti, et al., *Int. J. Pharm.*, 103:55–67 (1994).

The Effect of Various Polymeric Coating Systems on the Dissolution and Tabletting Properties of Potassium Chloride Microcapsules, Chang and Rudnic, *Int. J. Pharm.*, 70:261–270 (1991).

Company Monograph, Colorcon, Tastemasking Coating of Acetaminophen Granules, West Point, PA (technical product flyer), 2 pp. (1992).

Company Monograph, Colorcon, Surelease 0601–78 Coating for Chlorpheniramine Maleate Non–pariels Compressed into Tablets, West Point, PA (technical product flyer), 3 pp. (1993).

(List continued on next page.)

*Primary Examiner*—James M. Spear
*Attorney, Agent, or Firm*—Klarquist Sparkman Campbell Leigh & Whinston, LLP

[57] ABSTRACT

Active agents comprising coated pellets which self seal if they are damaged are described. More specifically, an active agent, or bead coated with an active agent, is coated with a rate-release controlling polymer and a hydrophilic gel-forming material which forms a gel upon hydration. If the bead is compressed into a solid compact which damages the polymer coating, the hydrophilic substance gels upon exposure to an aqueous environment. The gel provides sufficient sealing of the damaged area in the polymer so that a useful control of drug release is retained in spite of the damage to the polymer. The pellets of the invention exhibit improved flow and compactability. The compacts can be formulated to disintegrate in the gastrointestinal tract, and also may result in either controlled release or immediate release of the active agent.

26 Claims, 4 Drawing Sheets

OTHER PUBLICATIONS

Compression of Microcapsules I: Effect of Excipients and Pressure on Drug Release, Prapaitrakul and Whitworth, *Drug Development and Industrial Pharmacy*, 15(12):2049–2053 (1989).

A Study of the Manufacture and in vitro Dissolution of Terbutaline Sulfate Microcapsules, Ruiz et. al., *Drug Development and Industrial Pharmacy*, 16(11):1829–1842 (1990).

Tablet Properties and Dissolution Characteristics of Compressed Cellulose Acetate Butyrate Microcapsules Containing Succinyl Sulfathiazole, Sayed and Price, *Drug Development and Industrial Pharmacy*, 12(4):577–587 (1986).

Compaction Studies on Beads: Compression and Consolidation Parameters, Schwartz et.al., *Drug Development and Industrial Pharmacy*, 20(2):3105–3129 (1994).

Effect of Different Excipients on the Tableting of Coated Particles, Torrado and Augsburger, *Int. J. Pharm.*, 106:149–155 (1994).

The Evaluation of Formulation and Processing Conditions of a Melt Granulation Process, McTaggert et. al., *Int. J. Pharm.*, 19:139–148 (1984).

Tablets of Metronidazole Microcapsules: Release Characteristics, Chemtob, et. al., *Int. J. Pharm.*, 29:83–92 (1986).

A Sustained Release Drug Delivery Systems Using Calcium Alginate Beads, Badwan et. et., *Drug Development and Industrial Pharmacy*, 11(2&3):239–256 (1985).

Sustained Release Dosage Forms of Microencapsulated Isoniazed, Jalsenjak et. al., *J. Pharm. Pharmacol*, 32:678–680 (1980).

Effect of the Drying Method on the Mechanical and Drug Release Properties of Pellets Prepared by Extrusion–Spheronization, Dyer, et al., *Drug Development and Industrial Pharmacy*, 20(20):3045–3068 (1994).

COMPACTABLE SELF-SEALING DRUG DELIVERY AGENTS

FIELD OF THE INVENTION

This invention concerns compactable drug compositions and methods for their manufacture.

BACKGROUND OF THE INVENTION

The need for compressing drug-containing beads into solid compacts, wherein the beads have been formulated to provide controlled drug release, is well recognized in the pharmaceutical industry. Two excellent reviews of the advantages and difficulties associated with forming compacts are provided by Ragnarsson [*Development of a New Controlled Release Metoprolol Product*, G. Ragnarsson, A. Sandberg, U. E. Jonsson, and J. Sjogren, Drug Development and Industrial Pharmacy, 13:1495–1509 (1987)] and Aulton [*The Strength and Compaction of Millispheres*, M. E. Aulton, A. M. Dyer, and K. A. Khan, Drug Development and Industrial Pharmacy, 20:3069–3104 (1994)].

It also is known that the process of compacting polymer-coated beads often ruptures the polymer coating. Béchard and Leroux studied the effect of particle size and the use of various excipients in maintaining polymer coat integrity. [Béchard, S. R.; Leroux, J. C., *Coated Pelletized Dosage Form: Effect of Compaction on Drug Release*, Drug Dev. Ind. Pharm. 18:1927–1944 (1992)]. They showed a loss of sustained release properties with compacted polymer-coated beads. This was confirmed by Maganti and Celik [Maganti, L.; Celik, M., *Compaction Studies on Pellets: II. Coated Pellets*, Int. J. Pharm., 103:55–67 (1994)]. Maganti and Celik concluded that regardless of the amount of coating applied, sustained release properties of the coated beads were lost when the beads were compacted. A review of the limited information available in the literature on microparticulate compaction is given by Celik (Celik, M. In *Multiparticulate Oral Drug Delivery*, Marcel Dekker, Inc., New York, pp. 181–215, 1994).

Aulton, et. al. describe a very complex methodology for matching the mechanical properties of millispheres and tablet diluents to produce compacts. They have shown that filling the void volume with powdered excipients is both necessary and complex when tabletting polymer-coated beads. The minimum amount of excipient required to efficiently fill the void space between millispheres in order to leave an excess to facilitate bonding and cushioning was found to be 40%. If less than 30% excipient was added there was incomplete tablet bonding. The best possible compact formulation following extensive research to maximize drug loading with a minimum use of excipients contained only 46% drug.

Related reports include:

(1) compaction of polymer-coated beads into tablets (Chang and Rudnic, *The Effect of Various Polymeric Coating Systems on the Dissolution and Tabletting Properties of Potassium Chloride Microcapsules*, Int. J. Pharm., 70:261–270, 1991; Company Monograph, Colorcon, Surelease 0601-78 coating for chlorpheniramine maleate nonpariels compressed into tablets, West Point, Pa., 1994; Maganti and Celik, *Compaction Studies on Pellets: II Coated Pellets*, Int. J. Pharm., 103:55–67, 1994; Juslin et.al., Pharm. Ind., 42:829, 1980);

(2) emulsion solvent evaporation to produce microcapsules (Prapaitrakul and Whitworth, Compression of microcapsules I: *Effect of Excipients and Pressure on Drug Release*, Drug Dev. Ind. Pharm., 15(12): 2049–2053, 1989; Ruiz et. al., *A Study of the Manufacture and in vitro Dissolution of Terbutaline Sulfate Microcapsules*, Drug Dev. Ind. Pharm., 16(11):1829–1842, 1990; Sayed and Price, *Tablet Properties and Dissolution Characteristics of Compressed Cellulose Acetate Butyrate Microcapsules Containing Succinyl Sulfathiazole*, Drug Dev. Ind. Pharm., 12(4):577–587, 1986);

(3) extrusion/maumerization technology for bead manufacture (Schwartz et.al., *Compaction Studies on Beads: Compression and Consolidation Parameters*, Drug. Dev. Ind. Pharm., 20(20):3105–3129, 1994);

(4) coated particle compacts (Torrado and Augsburger, *Effect of Different Excipients on the Tabletting of Coated Particles*, Int. J. Pharm., 106:149–155, 1994);

(5) melt granulation technique for individual dose units (McTaggert et. al., *The Evaluation of Formulation and Processing Conditions of a Melt Granulation Process*, Int. J. Pharm., 19,139–148, 1984); and (6) microencapsulation techniques (Chemtob, et. al., *Tablets of Metronidazole Microcapsules: Release Characteristics*, Int. J. Pharm., 29:83–92, 1986; Badwan et. al., *A sustained Release Drug Delivery System Using Calcium Alginate Beads*, Drug Dev. Ind. Pharm., 11(2&3):239–256, 1985; Jalsenjak et. al., *Sustained Release Dosage Forms of Microencapsulated Isoniazid*, J. Pharm. Pharmacol, 32:678–680, 1980).

Most of the materials described in these documents require using cushioning agents. The cushioning agents are powders which are mixed with the polymer-coated beads or particles before compression into a tablet. This mixing leads to a major manufacturing problem which has not been stressed in the literature, i.e., segregation of polymer-coated beads or granules from cushioning excipients during normal production of compacts. Laboratory samples can easily be prepared by hand loading each die during production of a single tablet, but different size materials segregate in process scale-up (Chowan, *Segregation of Particulate Solids, Part I*, Pharm. Technol., 19(5):56–70, 1995; Chowan, *Segregation of Particulate Solids, Part II*, Pharm. Technol. 19(6):80–94, 1995).

Use of microcrystalline cellulose as a cushioning agent in powder form (Celic and Maganti, and Maganti and Celik), in the form of spheres (Prapaitrakul and Whitworth), and as granules (Torredo and Whitworth) has been investigated for preventing polymer coat fracture. It was thought that mixing placebo spheres of the same size as polymer-coated spheres would solve the segregation problem. However, as investigated by Aulton et. al., the use of placebo spheres requires considering additional factors, such as density and sphere strength. The authors also suggest segregation can occur upon scale-up.

Ragnarsson et. al. report large scale production of rapidly disintegrating tablets of polymer-coated beads mixed with tablet-forming excipients, but there was no mention of how the segregation problem was solved. The drug dose was relatively small and the compact contains about three times as much excipient as drug, which is not possible for moderate to large dose drugs. Thus, with Ragnarsson's invention, relatively large amounts of excipients are required to fill void volumes. This means that the compacts also are relatively large. Moreover, the drug dosing that can be obtained decreases as the amount of excipients increases.

In summary, if there are insufficient inert diluents separating polymer-coated beads then the beads come into direct contact and stick together to form a nondisintegrating matrix, and the polymer coat ruptures during compaction into tablets. Thus, although the initial composition may be formulated so that the beads control drug release, the nondisintegrating matrix formed by compressing the initial product controls drug release, not the original polymer coating as desired. If the matrix tablet formed disintegrates or is disrupted, a controlled or sustained release of drug is no longer maintained.

If there are sufficient inert diluents to keep the polymer beads separated during compaction, then only relatively small amounts of drug loading are possible. The polymer coating on the beads still ruptures (in most cases). Thus, it currently is believed that compacting known compositions, despite the amount of diluent used, results in loss of controlled drug release for disintegrating compacts. As a result, a need exists for polymer-coated compositions that can be compacted without forming a nondisintegrating matrix.

SUMMARY OF THE INVENTION

The present invention describes polymer-coated beads that can be treated to result in controlled drug release following compaction without using large amounts of diluents or cushioning agents to prevent polymer rupture. Polymer rupture still may occur, but control of drug release is maintained by treating the polymer-coated bead with a hydrophilic gel-forming agent. This discovery is easier to employ than known methods, and does not require any elastic or tensile strength measurements. Such measurements may be beneficial in optimizing a drug product formulation, but are not required.

The method disclosed herein allows using a polymer coat for its desirable properties other than matched mechanical properties, i.e. ease of application, stability on storage, diffusional resistance characteristics, costs, etc. Furthermore, the invention allows relatively large or small amounts of drug loading as desired, without requiring large percentages of cushioning agents to prevent rupture of the polymer coated beads. The invention provides the advantage of being able to formulate a rapidly disintegrating compact which can release individual drug-containing millispheres into the gastrointestinal tract. The invention also allows formulation of controlled-release compacts which can be crushed prior to swallowing while retaining an acceptable control of drug release. Such controlled-release compacts have not been previously known.

One embodiment of the present invention concerns drug delivery pellets that comprise a core portion and a coating. The core portion comprises an active agent, or a bead coated with an active agent. The coating and core portion form a discrete body, as opposed to a matrix that completely surrounds all of the pellets when the pellets are compacted into tablets. The coating comprises a hydrophilic gel-forming agent and a polymeric rate-controlling material.

The coating may comprise a single layer that includes a mixture of hydrophilic gel-forming agent and polymeric rate-controlling material. Alternatively, the coating may comprise a first hydrophilic gel-forming layer, the gel-forming layer being overcoated with the polymeric-rate controlling material. In still another embodiment, the coating may comprise a first polymeric rate-controlling material layer, the polymeric rate-controlling layer being overcoated with a second layer comprising a hydrophilic gel-forming layer.

Plural pellets can be compacted into tablets, and such tablets may be chewable. The pellets also may be formulated for delivering an active agent to a particular site, such as the lower gastrointestinal tract, which is defined as any site below the duodenum. Such site-specific delivery may be accomplished by formulating tablets to have a particular disintegration time. For example, delivering an active agent to the lower gastrointestinal tract generally means using a tablet that does not disintegrate for from about 3 hours to about 12 hours after ingestion. Examples of active agents that can be delivered to the lower gastrointestinal tract include, without limitation, proteins, polypeptides, and combinations thereof.

A method for forming disintegrating tablets also is an aspect of this invention. The method involves forming an active-agent delivery pellet. The pellet is then compressed into disintegrating tablets. Another embodiment of the method concerns forming compactable pellets having at least two distinct material layers. The method involves forming a pellet that includes a core portion comprising an active agent, or a bead coated with an active agent. The core portion is then spray-coated with excipients. This spray-coated composition is then compacted to form a disintegrating compact.

DETAILED DESCRIPTION OF THE PREFERRED EMBODIMENTS

Figure 1:
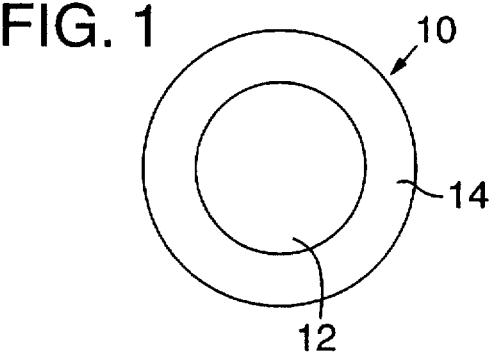
FIG. 1 is a schematic drawing illustrating a first embodiment of drug delivery compositions made according to the present invention.

The following term definitions are provided solely for the benefit of the reader, and should not be construed to limit the terms to any specific examples provided, or to be definitions which would be narrower than accepted by persons of ordinary skill in the art.

Active agent means any therapeutic or diagnostic agent now known or hereinafter discovered that can be formulated as described herein. Examples of therapeutics, without limitation, are listed in Urquhart's U.S. Pat. No. 4,649,043. Additional examples are listed in the *American Druggist*, p. 21–24 (February, 1995).

Diagnostic means, without limitation, a material useful for testing for the presence or absence of a material or disease, and/or a material that enhances tissue imaging.

Spheres, millispheres, pellets and particulates are terms which are interchangeable when referring to the drug delivery systems of this invention.

Controlled release includes timed release, sustained release, delayed release and all terms which describe a release pattern other than immediate release.

A core portion is the center portion of a layered drug delivery system. The core portion typically comprises active agent(s), either with or without added excipients, and also includes bead, such as sugar beads, coated with an active agent.

Drug delivery systems of the present invention comprise pellets that are discrete bodies. That is each pellet of the system constitutes a separate entity prior to compaction, and is not surrounded by a continuous encompassing matrix, such as the hydrogel reservoir taught by Urquhart et al.'s U.S. Pat. No. 4,649,043.

A disintegrating compact is a compact where no insoluble tablet-shaped device remains to be excreted or removed from the body after transport through the GI tract, and the original intact compact shape is not retained in a USP paddle dissolution test after 12 hours of treatment in gastrointestinal fluids.

Hydrophilic gel-forming materials or agents, also referred to as hydrogels, are materials which hydrate in water and exhibit the ability to retain a significant fraction of water within its structure. For purposes of this disclosure, these are materials which obtain a sufficiently viscous consistency capable of at least partially blocking cracks or openings in ruptured polymer coatings. The hydrogels can be non-crosslinked or they may be cross-linked with covalent or ionic bonds. The hydrogels can be of plant or animal origin, hydrogels prepared by modifying naturally occurring structures, and synthetic polymeric hydrogels.

Examples of hydrophilic gel-forming agents, without limitation, include materials like acacia, tragacanth, guar gum, pectin, xanthan gum, locust bean gum, Carbopol® acidic carboxy polymer, hydroxypropyl methyl cellulose, polycarbophil, polyethylene oxide, poly(hydroxyalkyl methacrylate), poly(electrolyte complexes), poly(vinyl acetate) cross-linked with hydrolyzable bonds, water-swellable N-vinyl lactams polysaccharides, natural gum, agar, agarose, sodium alginate, carrageenan, fucoidan, furcellaran, laminaran, hypnea, eucheuma, gum arabic, gum ghatti, gum karaya, arbinoglactan, amylopectin, gelatin, hydrophilic colloids such as carboxylmethyl cellulose gum or alginate gum, including both non-crosslinked and crosslinked alginate gums, wherein the crosslinked alginate gums may be crosslinked with di- or trivalent ions, polyols such as propylene glycol, or other crosslinking agents, Cyanamer® polyacrylamides, Good-rite® polyacrylic acid, starch graft copolymers, Aqua-Keeps® acrylate polymer, ester crosslinked polyglucan, and the like. Some of these hydrogels are discussed in U.S. patents, U.S. Pat. Nos. 3,640,741, 3,865,108, 3,992,562, 4,002,173, 4,014,335, and 4,207,893. Hydrogels also are discussed in the *Handbook of Common Polymers*, by Scott and Roff, published by the Chemical Rubber Company, Cleveland, Ohio.

Overcoating refers to applying at least one coat, and perhaps plural coats, over a core portion of a drug delivery system. Materials suitable to overcoat include, but are not limited to, polymeric rate-controlling materials, hydrophilic gel-forming materials, therapeutics, diagnostics, typical tablet excipients or diluents such as direct compression binders, disintegrants, fillers, flavors, colors, lubricants, and other materials such as active ingredients which may be the same or different than the first active ingredient. The invention allows for immediate release of active ingredient from an outer coat while an interior active ingredient may have a controlled release.

A polymer coating agent is a material applied as a film to control drug release, and may also be referred to herein as a polymeric rate-release or rate-control materials. Polymeric coating agents include, without limitation, diffusional controlled release polymers, erodible polymers, and enteric coating polymers. The polymeric coating material also may be a bioerodible material that bioerodes at a controlled rate.

Polymer coating agents used in this manner include, but are not limited to, polymethacrylates, ethylcellulose, silicone elastomers, ethylene-vinyl acetate, polyethylene, cross-linked polyvinyl pyrrolidone, vinylidene chloride-acrylonitrile copolymer, polypropylene, polyvalent acid or alkali mobile crosslinked polyelectrolytes, polycarboxylic acid, polyesters, polyamides, polyimides, polylactic acid, polyglycolic acid, polyorthoesters, polyortho-carbonates, and the like. Such polymers, and procedures for forming coatings using the polymers, are disclosed in U.S. patents, U.S. Pat. Nos. 3,811,444, 3,867,519, 3,888,975, 3,971,367, 3,993,057 and 4,138,344. Such materials can be applied using methods known in the art, such as the methods described in U.S. patents, U.S. Pat. Nos. 3,938,515, 3,948, 262, and 4,014,335.

Any of the foregoing polymeric materials may be used alone to form polymeric coatings. Polymeric materials also may be used in combination, i.e. two or more different polymeric materials may be combined. Moreover, the polymeric materials also may be combined with other materials. For example, polymer-coating materials may also contain placticizers, such as triethylcitrate or dibutyl sebacate, among many others as well known in the art. Polymer coatings may be applied as aqueous dispersions or in organic solvents.

Both polymer rate-control agents and hydrophilic gel-forming agents are commonly referred to as polymers. However, as referred to herein "polymeric materials" refers to rate-controlling materials. Moreover, for purposes of the present invention, rate-controlling materials and hydrophilic gel-forming agents also are differentiated in terms of their behavior or use.

FIG. 1 illustrates one embodiment of a compactable drug-delivery system 10. Delivery system 10 comprises core portion 12 and coating layer 14. Core portion 12 generally comprises a therapeutic, a mixture of therapeutics, a diagnostic, a mixture of diagnostics, or a mixture comprising a diagnostic or a therapeutic. Core portion 12 also may comprise a bead, such as a sugar bead, coated with a therapeutic, a mixture of therapeutics, a diagnostic, a mixture of diagnostics, or a mixture comprising a diagnostic and a therapeutic.

Surrounding core portion 12 is coating layer 14. In the embodiment illustrated in FIG. 1, layer 14 comprises a mixture of a hydrophilic gel-forming agent and a polymeric rate-controlling material. The relative proportions of each of these materials in layer 14 is dependent upon the characteristics desired in the end product. One object of the present invention is to provide a composition which, when compressed, does not form a nondisintegrating matrix. Thus, the relative amounts of hydrophilic gel-forming agent and polymeric rate-controlling material should be chosen so that the product can be efficiently compressed, and so that the compression does not form a nondisintegrating matrix. A plurality of delivery systems 10 may be compressed together to form a tablet. When such a tablet is crushed, such as by a patient between two spoons, by chewing or with a pill crusher, cracks may form in the polymeric rate-controlling material. There should be sufficient hydrophilic gel-forming agent to at least partially seal any such cracks that form upon exposure to an aqueous environment. This prevents core portions 12 of adjacent drug delivery systems 10 from coming into contact during compression or crushing by a person taking the composition.

It currently is believed that, with respect to the weight of a coating layer, less than about 1 weight percent polymeric rate-controlling material may be sufficient to obtain a desired drug-release profile. Alternatively, the rate-controlling material may be used in much larger quantities, such as up to about 99 weight percent. Moreover, it currently is believed, with respect to the weight of a coating layer comprising a mixture of polymeric rate-controlling material and hydrophilic gel-forming material, that the combined weight percent of hydrophilic gum and polymeric rate-controlling material is from less than about 1 weight percent to about 99 percent, and may be from about 1 percent to about 50 weight percent. Is should be understood that the mixed layer also may include additional materials, such as excipients. One of ordinary skill in the art can determine the relative proportions of rate-controlling material and hydrophilic gel-forming material in layer 14, based on, amongst other things, the desired results.

Figure 2:
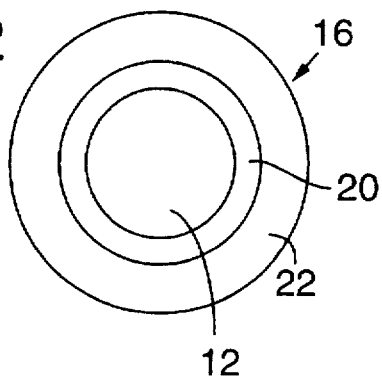
FIG. 2 is a schematic drawing illustrating a second embodiment of a drug delivery system comprising active agents overcoated with plural, distinct coating layers.

FIG. 2 illustrates another embodiment of a drug delivery system 16 made according to the present invention. The delivery system 16 comprises a core portion 12 as with the embodiment illustrated in FIG. 1. However, instead of having a layer 14 comprising a mixture of hydrophilic gel-forming agent and polymeric rate-controlling material, delivery system 16 comprises a first hydrophilic gel-forming layer 20 that coats core portion 12. The gel-forming layer 20 is then overcoated with a polymeric rate-controlling material layer 22. One concern is that if the polymer coats come into direct contact with each other, upon compression interlocking polymer coats may form to produce a nondisintegrating matrix. To maintain discrete bodies, additional outercoatings of, without limitation, excipients or active agents, generally are placed as the outermost coat instead of the polymeric rate-controlling material. When plural delivery systems 16 are compacted, and should a polymeric rate-controlling layer 22 be ruptured, the adjacent layer 20 hydrates upon contact with an aqueous environment to at least partially fill any cracks that may have formed in layer 22.

Figure 3:
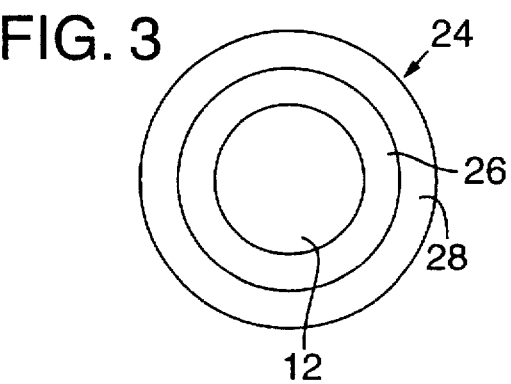
FIG. 3 is a schematic drawing illustrating a third embodiment of a drug delivery system comprising active agents overcoated with plural, distinct coating layers.

FIG. 3 illustrates still another embodiment of the present invention. FIG. 3 illustrates a delivery agent 24 comprising a core 12 surrounded by a first polymeric rate-controlling layer 26. Rate-controlling layer 26 is then overcoated with a hydrophilic gel-forming material layer 28. Thus, upon compaction of plural drug-delivery systems 24 and subsequent exposure to an aqueous environment, any cracks that form in the polymeric rate-controlling layers 26 would be at least partially filled with the hydrophilic gel-forming material from the adjacent layer 28. In general, it currently is believed that placing the hydrophilic gel-forming material as the outermost coat for delivery systems as described herein may be operational, but that this is not the best arrangement for formulating drug delivery systems. One concern is that, upon exposure to an aqueous environment, the outer layer of gel-forming material of multiple adjacent agents 24 may connect and form an encompassing matrix. Thus, to maintain discrete bodies, additional outercoatings of, without limitation, excipients or active agents, generally are placed as the outermost coat instead of the hydrophilic gel-forming agent.

Figure 4:
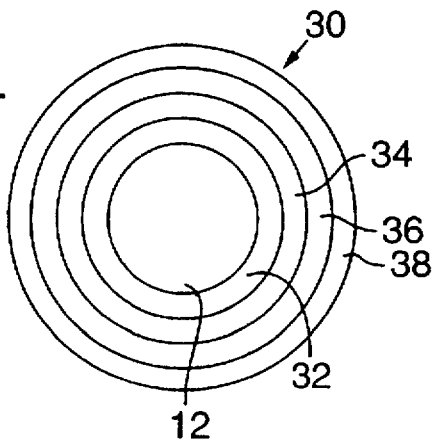
FIG. 4 is a schematic drawing illustrating a fourth embodiment of a drug delivery system comprising plural coating layers.

FIG. 4 illustrates a drug-delivery system 30 having an overcoating comprising plural layers of polymeric rate-controlling materials and hydrophilic gel-forming agents. FIG. 4 illustrates delivery agents 30 having a first coating layer comprising a polymeric rate-controlling material 32. Layer 32 is overcoated with a layer 34, comprising a hydrophilic gel-forming agent. FIG. 4 further illustrates that layer 34 has an overcoating 36 comprising a polymeric rate-controlling material. Finally, FIG. 4 illustrates that the drug-delivery agent 30 may include an outer layer 38 comprising a hydrophilic gel-forming agent. As before, the outer layer of hydrophilic gel-forming agent may be covered with additional excipients, active agent(s), or both.

With further reference to FIG. 4, it should be understood that the arrangement of layers 32–38 may be changed. For instance, layer 32 may comprise a hydrophilic gel-forming agent instead of a polymeric rate-controlling material. In other words, the present invention should not be limited to the order of layers illustrated in FIG. 4 because the arrangement of these layers can be altered from that illustrated in FIG. 4. It also should be understood that two polymeric rate-controlling materials could be placed adjacent each other, with a hydrophilic gel-forming agent either serving as an undercoat or as an overcoat to these adjacent, but distinct, polymeric rate-controlling materials. Moreover, the individual polymeric rate-controlling material layers could comprise various combinations of polymeric rate-controlling materials formulated to provide a desired result. Similarly, plural different hydrophilic gel-forming agents could be formulated to form a distinct layer adjacent one or more polymeric rate-controlling materials. Finally, as illustrated in FIG. 1, plural but distinct layers comprising mixtures of polymeric rate-controlling materials and hydrophilic gel-forming agents could be used to coat core portions 12, or as any of the plural layers.

The following examples are provided to illustrate certain features of the present invention. These examples should not be construed to limit the present invention to the particular features stated in these examples.

EXAMPLE 1

Figure 5:
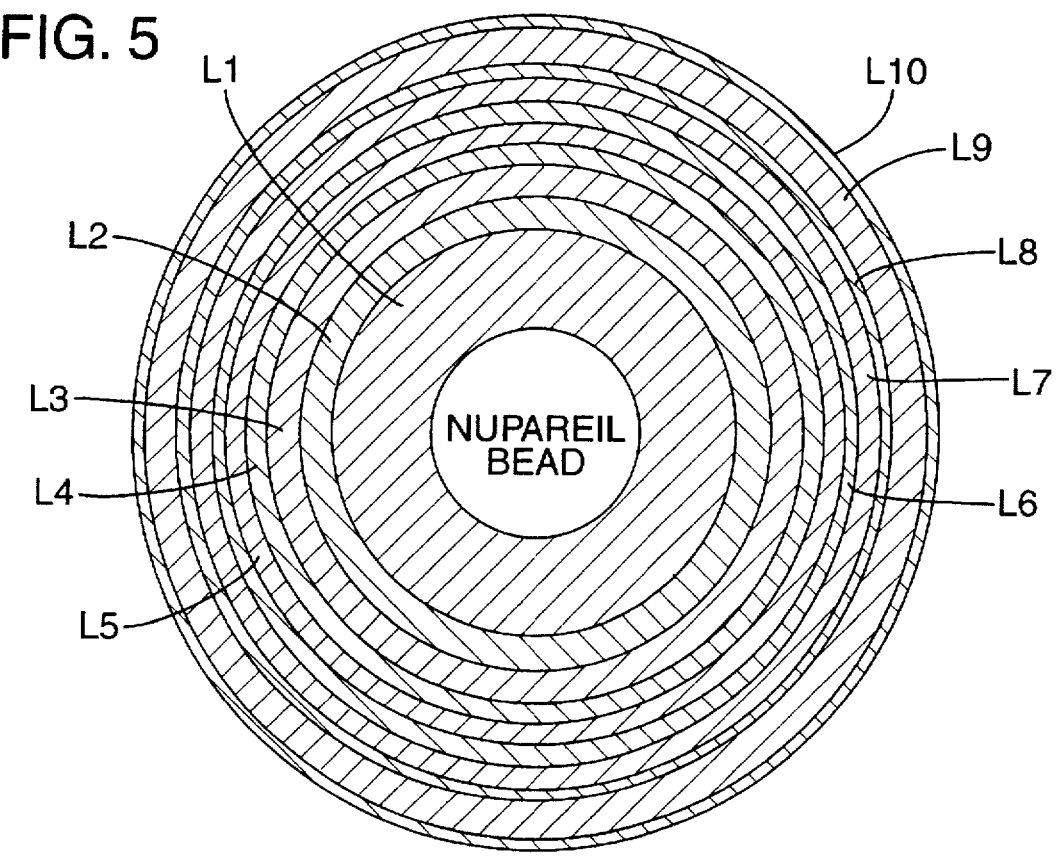
FIG. 5 is a schematic drawing illustrating a drug delivery system comprising ten distinct layers, $L_1$–$L_{10}$.

The purpose of this example was to evaluate the effects of compressing a new composition using multi-layer beads with alternating multiple layers of polymer and drug or excipients. FIG. 5 is a schematic representation of a bead having 10 alternating layers of drug and polymer coat on a core comprising a nonpareil sugar bead.

A. Coating Procedure

A weighed amount (100 g) of Nu-Pariel sugar beads were placed into the coating chamber of a fluid-bed spray coater with an Aeromatic® chamber over a Wurster column insert and fluidized for 20 minutes to equilibrate the temperature (40° C.) of the coating process. A solution of drug (acetaminophen, APAP) was prepared in ethanol (95%) using [hydroxypropyl cellulose:polyvinyl pyrrolidone (1:2)] as binders. The drug solution was then sprayed onto the beads. A 6% w/w polymer coat (Aquacoat® with 30% plasticizer, dibutyl sebacate (DBS):triethyl citrate [(TEC), 1:1)] was applied over each drug layer on the beads. A 20 minute curing time at 40° C. was allowed after each coating layer. As multiple layers were applied to each batch of beads, layers which were 6% of previous batches becomes a smaller percent of the final product. This process of alternating drug and polymer layers was repeated until the last layer (layer 10) of polymer coat was applied (see FIG. 5). In layer 9, 14% w/w mannitol replaced the drug.

B. Bead Compaction and Dissolution Testing

Caplets (100 mg-capsule shaped tablets) were made on a Carver hydraulic press. The beads were compressed without the addition of any filler material and empirical observation showed them to have excellent flow characteristics. Dissolution studies on the uncompacted and compacted beads were conducted using USP dissolution apparatus II at 50 rpm with simulated intestinal fluid (pH 7.4±0.1) maintained at 37°±0.5° C. Samples (5 ml aliquot) were collected with replacement. Samples were analyzed with a UV spectrophotometer at $\lambda=244$ nm after filtration and proper dilution. All dissolution experiments were done in duplicate. The maximum standard deviation observed for any batch was not more than 5%.

C. Scanning Electron Microscopy (SEM)

An AmRay (model 1000A) microscope at an accelerating voltage of 10 kV was used for SEM. Samples for SEM were prepared by freezing the beads and caplets in liquid nitrogen and then fracturing the beads in a mortar with a pestle. Samples also were prepared simply by slicing the beads and caplets with radon blades. The samples were then coated with a 60:40 gold/palladium alloy prior to microscopic examination. The samples prepared by the two different techniques produced similar SEM results.

Figure 6:
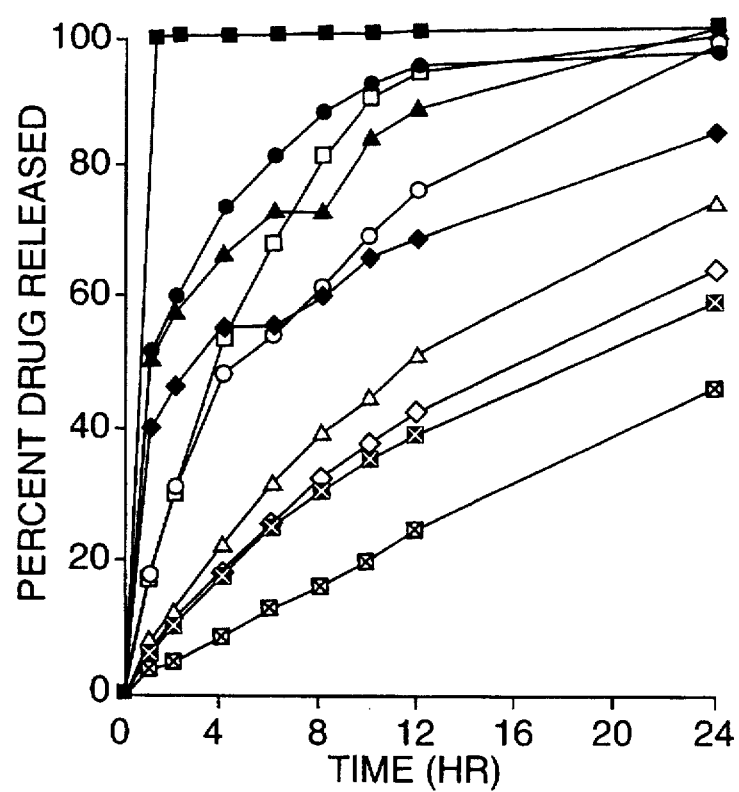
FIG. 6 is a graph showing percent drug release versus time for noncompacted multilayered beads.

SEM photomicrographs showed each drug or polymer section as distinct, prominent layers. Table 1 shows the composition of each layer. Percent drug release versus time profiles for non-compacted multi-layered beads are plotted in FIG. 6 (FIG. 6 shows percent drug release versus time profiles for noncompacted multilayered drugs: ■=L1, □=L2, ●=L3, ○=L4, ▲=L5, △=L6, ◆=L7, ◇=L8, dark-filled ballot box=L9, and ⊠=L10). As expected, the percent drug release rate decreases as the amount of coating increases, with only 43% of drug being released in 24 hours for the highest level coated beads (L10). Beads with an outer layer of drug (L1, L3, L5, L7) release drug at a faster rate even when there is a 6% w/w polymer coat underneath the final drug layer.

The multi-layered beads were then compressed into caplets at 500 lb force without any additional tabletting excipients. Beads with 5 to 10 layers (Table 1) were used to study drug release behavior following compaction of the multi-layered beads. Upon compaction, discrete beads still can be clearly distinguished within the caplet. Significant deformation of the beads is observed in SEM and cracks in some polymer layers can be observed in SEM.

Radebaugh et al (U.S. Pat. No. 4,820,522) teach the need for a controlled release formulation of APAP. A primary advantage of their invention is that their non-disintegrating tablets are bioerodible when swallowed. That is, no insoluble tablet shaped device remains to be excreted or removed from the body after acetaminophen (APAP) is depleted from the tablet. Tylenol ER is marketed in the United States and is labeled with the Radebaugh U.S. Pat. No. 4,820,522. Dissolution of this product in the USP paddle dissolution apparatus with two hours of gastric fluid followed by two hours of intestinal fluid results in dissolution of 50% of the dose in about 20 minutes, 70% dissolution in about 50 minutes, and is over 90% dissolved in about 1.5 hours. These results are consistent with data in Table 2a of U.S. Pat. No. 4,820,522 which show a maximum plasma concentration of APAP at 1.5 hours post dosing.

Figure 8:
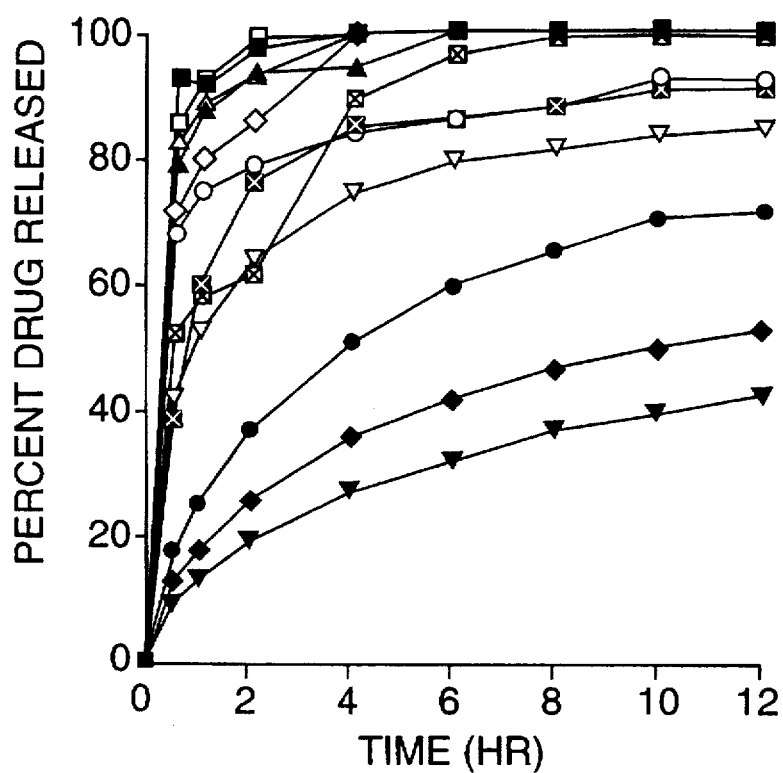
FIG. 8 is a graph illustrating the effect of drug release from intact and crushed caplets made according to the present invention.

Results for the layer 9 beads, containing mannitol as the outer layer, show similar dissolution of the active ingredient (APAP) for both intact caplets and crushed caplets (FIG. 8). The intact caplet disintegrated in about 20 minutes in the dissolution fluid. FIG. 8 [IC=intact caplets; CC=crushed caplets; ■=L5(ic), □=L5(cc), ●=L6(ic), ○=L6(cc), ▲=L7(ic), △=L7(cc), ◆=L8(ic), ◇=L8(cc), dark-filled ballot box= L9(ic), ⊠=L9(cc), ▼=L10(ic), and ▽=L10(cc)], shows dissolution of APAP from the disintegrating compact was 50% in about 50 minutes, 70% dissolved in about 100 minutes, and 90% dissolved in about 10 hours. The crushed caplet for

TABLE 1

| Ingredient | L1 % | L2 % | L3 % | L4 % | L5 % | L6 % | L7 % | L8 % | L9 % | L10 % |
|---|---|---|---|---|---|---|---|---|---|---|
| Beads | 56.0 | 52.6 | 43.3 | 40.9 | 34.0 | 32.0 | 26.9 | 25.3 | 21.6 | 20.3 |
| APAP 1 | 44.0 | 41.4 | 34.2 | 30.5 | 24.2 | 23.0 | 19.0 | 17.5 | 15.2 | 14.3 |
| AC 1 |  | 6.0 | 4.9 | 4.7 | 3.9 | 3.6 | 3.1 | 2.9 | 2.5 | 2.3 |
| APAP 2 |  |  | 17.6 | 18.2 | 14.9 | 14.0 | 11.6 | 11.0 | 9.3 | 8.6 |
| AC 2 |  |  |  | 5.7 | 4.7 | 4.4 | 3.7 | 3.5 | 3.0 | 2.8 |
| APAP 3 |  |  |  |  | 18.3 | 17.0 | 14.0 | 13.2 | 11.0 | 10.4 |
| AC 3 |  |  |  |  |  | 6.0 | 5.1 | 4.8 | 4.0 | 3.8 |
| APAP 4 |  |  |  |  |  |  | 16.6 | 15.8 | 13.4 | 12.7 |
| AC 4 |  |  |  |  |  |  |  | 6.0 | 5.1 | 4.8 |
| M |  |  |  |  |  |  |  |  | 14.9 | 14.0 |
| AC 5 |  |  |  |  |  |  |  |  |  | 6.1 |

L = layer on bead, APAP = acetaminophen, APAP solution for all layers was prepared in hydroxypropyl cellulose (2.2%):polyvinylpyrrolidone (4.5%); M = mannitol; AC = Aquacoat ®, with 30% w/w plasticizer (dibutyl sebacate:triethyl citrate 1:1)

Figure 7:
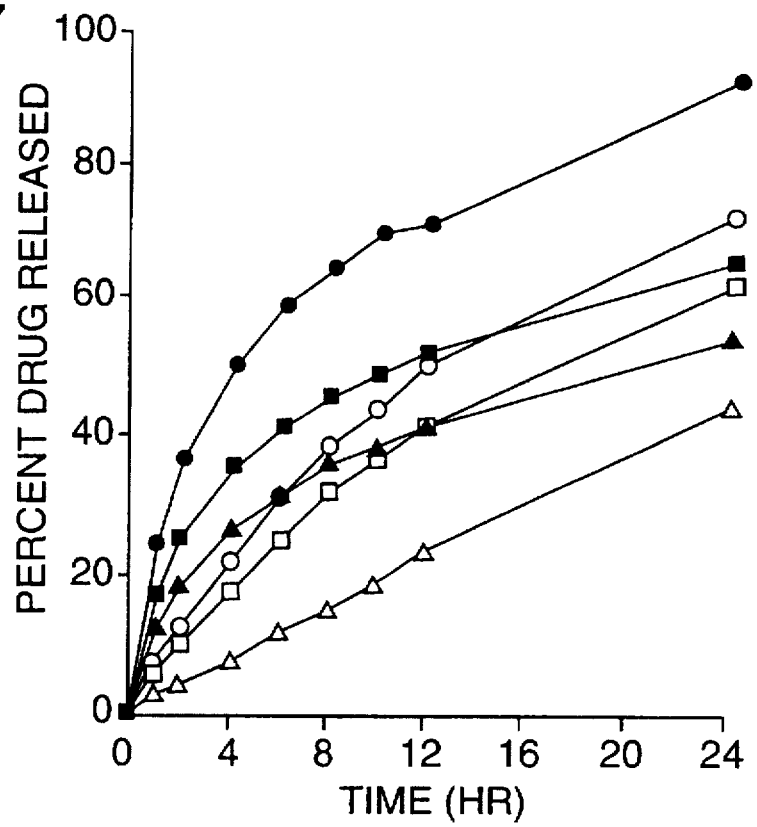
FIG. 7 is a graph illustrating dissolution profiles for compacted versus noncompacted drug delivery systems.

FIG. 7 [●=L6(caplet), ○=L6 (bead), ■=L8(caplet), □=L8(Bead), ▲=L10(caplet), △=L10(bead)] compares dissolution profiles of compacted (500 lb) and non-compacted beads for layered beads 6, 8, and 10, which had the polymer coat as the outermost layer. All these compacts shown in FIG. 7 became non-disintegrating matrix formulations providing sustained release of drug, but failing to disintegrate during 24 hours of dissolution testing. Release patterns show that compression resulted in an increase in drug release from caplets compared to non-compacted beads, indicating that at least some bead coatings were ruptured.

Intact caplets with an outer layer of drug on the beads disintegrated in 2–3 minutes. The caplet with mannitol as the outer layer disintegrated within 20 minutes. Some of the caplets made with multi-layered beads at 500 lb force were crushed with a pill crusher (from American Medical Industry, Highland Park, Ill.), and dissolution was conducted to compare release profiles of intact and crushed caplets (FIG. 8). Crushed caplets released drug more quickly than the original non-compacted beads (FIG. 8 vs. FIG. 6), indicating that many of the polymer coatings ruptured during compression.

the beads with mannitol as the outer layer release 50% APAP in about 30 minutes, 70% in about 2.7 hours and about 90% in just under 5 hours. This example therefore shows that polymer-coated drug particulates can contain one or more additional layers of drug and polymer coats and excipients and be directly compressed into a compact which will disintegrate in gastrointestinal fluids, providing a useful drug release pattern.

This invention has many advantages over the system described in U.S. Pat. No. 4,820,522. The '522 patent teaches preferably using a bi-layer tablet containing both an immediate-release and a sustained-release layer. Multiple-layer beads are easy to produce using standard spray-coating equipment but multiple-layer tablets require specialized tabletting equipment not routinely available in small companies. Both immediate-release and controlled-release drugs are provided by compressing one multiple-layered bead batch, but the '522 patent requires separate formulations for immediate release and controlled release. Direct compression of dry ingredients is preferred over granulation in manufacturing as wet granulation, drying, sieving, blending, and milling are all costly steps and errors can be introduced at each step. Particle sizes must be carefully controlled to avoid segregation during production. The current invention avoids all of these steps, but all are required for the products made according to the '522 patent. Further, the current invention produced a product wherein APAP release from the intact compressed caplet and the crushed caplet resulted in similar drug release. This is a distinct advantage over the teachings of the '522 patent since crushing the product of the '522 patent destroys the controlled release matrix. Crushing tablets prior to swallowing is advantageous for the elderly and pediatric population, and for many others who have trouble swallowing compacts.

EXAMPLE 2

Multi-layer beads with microcrystalline cellulose (Avicel® PH-101) as on outer layer were also prepared. Avicel® was coated as one big batch and samples were collected after 20, 40, 60 and 80% Avicel® w/w coating layers were applied, corresponding to layers 7, 8, 9 and 10, respectively, as shown in Table 2.

EXAMPLE 3

A nondisintegrating matrix produced by compressing beads having only 3.2% chlorpheniramine maleate (active ingredient), which had been coated with a polymer and then overcoated with polyethylene glycol(PEG)/microcrystalline cellulose mixture, has been reported [Colorcon Company monograph, Surelease 0601-78, coating for chlorpheniramine maleate non-pariels compressed into tablets at 10–20 kN force (14 kN=3,150 lb), West Point, Pa., 1994]. PEG is a readily deformable material (known as Carbowax®) and was used in order to minimize the risk of fracturing the polymer-coated beads.

Drug (APAP) loaded beads (40/60 mesh) were coated with 20% Aquacoat® (ethylcellulose polymer film) which provides a diffusional release barrier to control drug release. These beads were then spray coated with 20% w/w polyethylene glycol (PEG) 8000 as a cushioning agent to minimize fracture. The beads were compacted into caplets at 3,150 lb (14 kN) force. The compacts were nondisintegrating matrix formulations and drug release was approximately

TABLE II

| Ingredient | Layer No. | | | | | | | | | |
|---|---|---|---|---|---|---|---|---|---|---|
| | L1 % | L2 % | L3 % | L4 % | L5 % | L6 % | L7 % | L8 % | L9 % | L10 % |
| Beads | 56.0 | 52.6 | 43.3 | 40.9 | 34.0 | 32.0 | 25.6 | 19.2 | 12.8 | 6.4 |
| APAP 1 | 44.0 | 41.4 | 34.2 | 30.5 | 24.2 | 23.0 | 18.5 | 13.9 | 9.0 | 4.6 |
| AC 1 | | 6.0 | 4.9 | 4.7 | 3.9 | 3.6 | 2.9 | 2.2 | 1.5 | 0.7 |
| APAP 2 | | | 17.6 | 18.2 | 14.9 | 14.0 | 11.0 | 8.4 | 5.6 | 2.8 |
| AC 2 | | | | 5.7 | 4.7 | 4.4 | 3.5 | 2.7 | 1.8 | 0.9 |
| APAP 3 | | | | | 18.3 | 17.0 | 13.5 | 10.0 | 6.8 | 3.54 |
| AC 3 | | | | | | 6.0 | 4.8 | 3.6 | 2.4 | 1.2 |
| AV 1 | | | | | | | 20.2 | 17.3 | 14.7 | 12.4 |
| AV 2 | | | | | | | | 22.7 | 19.3 | 16.3 |
| AV 3 | | | | | | | | | 26.1 | 22.0 |
| AV 4 | | | | | | | | | | 29.2 |

L = layer on bead, APAP = acetaminophen, APAP solution for all layers was prepared in hydroxypropyl cellulose (2.2%):polyvinylpyrrolidone (4.5%); M = mannitol; AC = Aquacoat ®, with 30% w/w plasticizer (dibutyl sebacate:triethyl citrate 1:1); AV = Avicel ® PH-101.

The new L7 and L8 beads with outer coats of 20% or 40% Avicel® were compressed at 100 lb force and the beads with more Avicel® were compressed at 500 lb force. A mixture of different percentage Avicel® coated beads were also compacted. For some combinations of Avicel® coated beads, a force of 500 lb. rather than 100 lb. was required to produce physically stable caplets. The Avicel® coating on beads did not produce any significant effect on drug release compared to earlier results, from either non-compacted or compacted beads. Thus, Avicel® did not eliminate rupture of polymer coating on beads during compaction.

However, a sufficient amount of coatings remained in place to control release of drug such that there was 70% release at about 50 minutes and 90% release took about 2 hours to 6 hours. These compacts readily disintegrate (less than 20 minutes in the dissolution test) and can be crushed prior to swallowing. This is of significant value for the many elderly and pediatric patients who have difficulty swallowing. The 1994 Red Book in the Clinical Reference Guide section, p. 21–22, lists over 250 commercially available drug products which should not be crushed. The invention disclosed herein can be used for these and other drugs to produce solid dosage forms which can be crushed prior to administration if desired. This example is consistent with Example 1 and shows significant improvement over the teachings of the '522 patent while providing some immediate release of drug and controlled release of drug from a disintegrating compact.

zero order from two hours onward with less than 20% drug release in the first two hours.

APAP beads coated with 20% controlled release polymer and overcoated with 20% PEG 8000 were then handmixed with a further 5% super disintegrant (Explotab® brand sodium starch glycolate). The super disintegrant was observed to segregate from the beads. An additional formulation was prepared having 20% controlled release polymer spray layered with 20% PEG 8000, and then spray layered with 10% Avicel® PH-101, followed by spray layering 5% Explotab®. Beads were then compressed into caplets at 125–1000 lb force. The compacts produced when Explotab® was handmixed with the beads but no Avicel® began to disintegrate within one-half hour and were completely disintegrated into individual beads within 2 hours; approximately 80% of the drug was released at time 4 hours.

Figure 9:
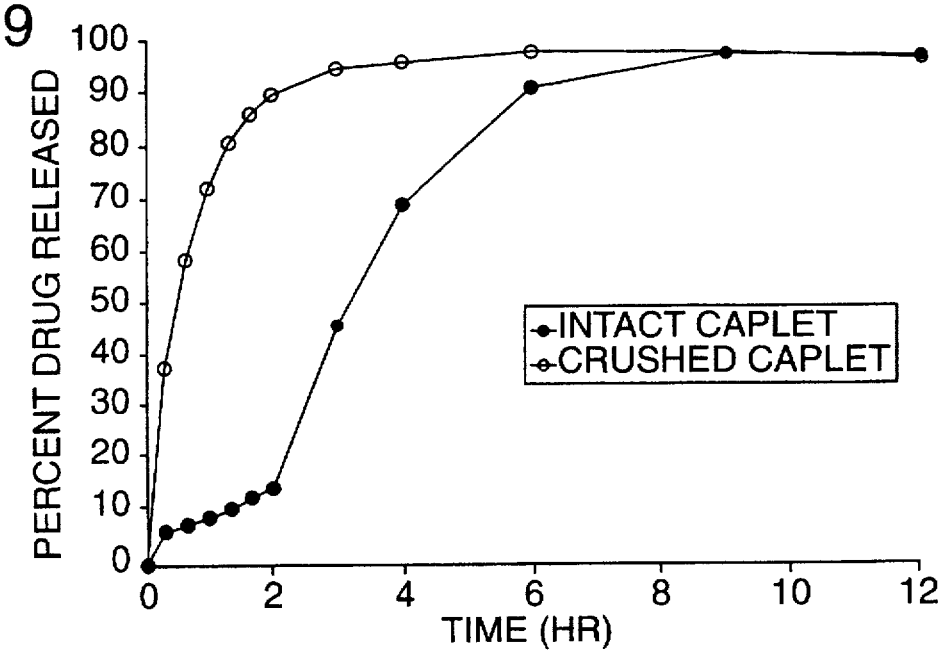
FIG. 9 is a graph illustrating the percent drug release from intact and crushed caplets.

For intact caplets, the compacts with spray layered Avicel® disintegrated immediately on transfer from gastric fluid into intestinal fluid, demonstrating an immediate release and a controlled release portion of drug with total drug being dissolved in 6–8 hours (FIG. 9). The caplets were crushed as previously described and release of drug was very rapid (FIG. 9) which indicates the polymer coat on the beads was ruptured during the compaction. Thus, the PEG cushioning agent is not able to prevent polymer coat rupture.

Thus, the results provided in FIG. 9 show that PEG provides no advantage in protecting against polymer-coat rupture during compaction. PEG also has the disadvantage of producing a non-disintegrating matrix tablet. Non-disintegrating matrix tablet formulations cannot provide a readily flexible or adjustable ratio of immediate release portion of drug to sustained release portion of drug. The current invention allows for controlling the ratio of immediate release of drug relative to controlled release of drug through selection of the layer(s) containing drug. Different amounts or ratios of active ingredients can be "buried" in the core or applied only to the surface layer if desired to obtain a preferred drug release rate.

With the current invention, small doses of drug such as chlorpheniramine can be time delayed by burying the drug in an inner layer of the particulate. Application of the current invention through addition of a layer of super disintegrant or microcrystalline cellulose results in a disintegrating compact with a desirable drug release profile.

EXAMPLE 4

Nonpareil sugar beads were covered with a single layer of drug (APAP) using procedures similar to those of Example 1. These beads were then coated with a 9% base coat of ethylcellulose (Aquacoat® as in Example 1).

A polyethylene oxide (Polyox N-3000) solution was then spray layered to 10% weight gain over the Aquacoat® seal-coat, followed by another 10% w/w Aquacoat® layer over the polyethylene oxide (PEO) layered beads. 10% Avicel® Ph-101 (microcrystalline cellulose as a direct compression agent) was applied as the next layer, and then and an outermost layer of 5% w/w disintegrant (Explotab®) was applied.

Figure 10:
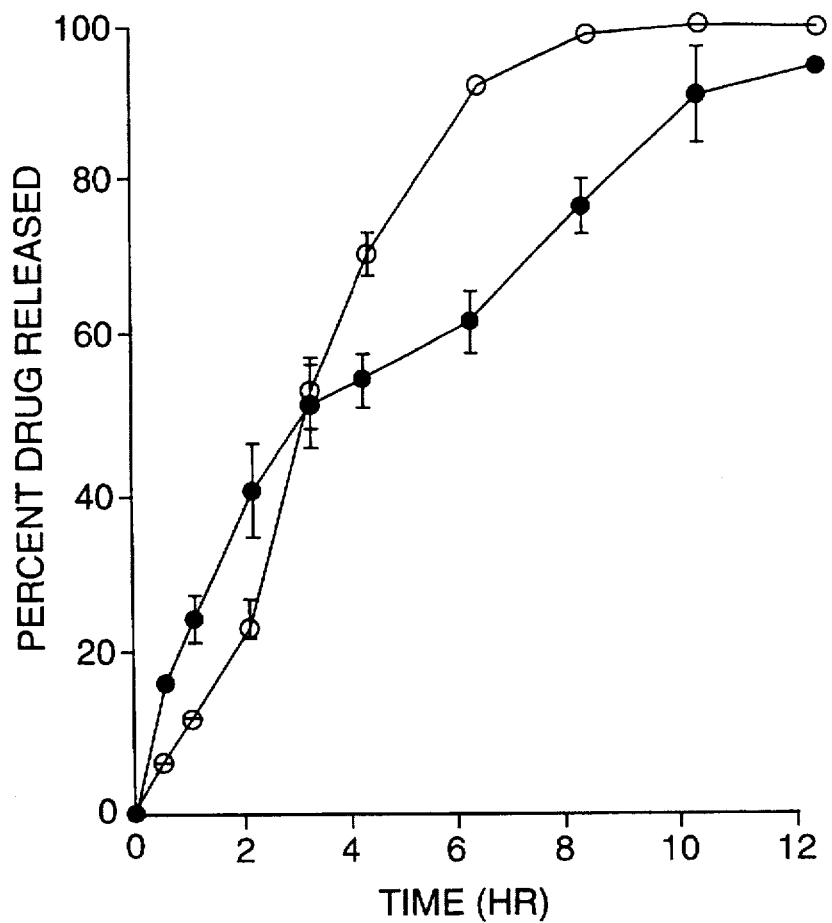
FIG. 10 is a graph illustrating percent drug release versus time for drug delivery systems made according to the present invention.

FIG. 10 shows the dissolution profile of spray coated PEO beads and caplets [●=uncompacted beads, ○=caplets at 1000 lb]. As evident from APAP dissolution profiles shown in FIG. 10, drug release from caplets is slower than from uncompacted beads for the first 2 hours. This is quite surprising since the caplets disintegrated into individual beads within 20 minutes; after 2 hours when the dissolution medium is changed from simulated gastric to intestinal fluid, an increase in the release rate from disintegrated caplets is observed with total drug released in about 8 hours.

The formulation in this example has not been optimized, yet the results are excellent. Ragnarsson reports that the stress induced when coating pellets into tablets may disrupt the coating membrane and an increase in particle size tends to give more rupture during tabletting. However, with an ethylcellulose coating of APAP beads the coating ruptures when compacting beads of initial size of about 45–60 mesh. All previous findings indicate that some of the ethylcellulose coating is ruptured in this experiment. The small amount of microcrystalline cellulose (Avicel® PH-101) is an excellent binder when applied as an overcoat on the beads and allows direct compression of the beads without the use of large amounts of diluents and filler, and avoids segregation problems which occur if different particle size materials are combined. In this case, only the final beads, and no additional powders, are needed for compression. The Explotab® acts as a disintegrant which causes the caplet to fall apart in an aqueous environment. The polyethylene oxide serves a very unique and previously unknown function in maintaining controlled release from compacted beads even though a nondisintegrating matrix tablet is not formed and the caplet formed does disintegrate rapidly in aqueous media.

While the exact mechanism is unknown, it is postulated that the polyethylene hydrates and forms a gel which acts as a sealant for the cracks which form in the ruptured polymer coating. Larger size drug beads can be used which means much larger amount of drug loading. In some cases, over 90% drug loading has been produced on sugar beads. Using larger beads means less polymer coat is needed to produce the same size thickness polymer coat and control of release because the larger beads have a smaller specific surface area.

Any hydrophilic gel-forming agent with sufficient rate of hydration and viscosity can be used. The hydrophilic gel forming agent can be sandwiched between polymer layers or applied below or over the polymer layer. The polymer layer may be a typical diffusional controlled release polymer film or an enteric coating film. Further optimization will be apparent to one skilled in the field. The beads can be made by spray layering or marumerization or spheronization as is known in the art. The process can be applied to granules or other discrete particles although it is recognized that coating of spheres requires less coating material than irregular particles. The amounts of hydrophilic gel and polymer coating agent can readily be optimized to apply to drugs with vastly different physical-chemical characteristics. Well known excipients such as anti-tack and lubricant agents can be used in spray coating as needed.

The invention described herein has many applications. The formulation process described may be employed for compacts to be used in, but not limited to, humans, animals, plants, bacterial or cell cultures, or outside of biological systems such as in diagnostic tests. The active ingredient may be a single agent or a mixture of active agents and may be drugs or other agents. The active ingredient may be released (1) in a controlled manner such that all is released very rapidly or (2) some or all is released slowly or (3) is time delayed. Beads may be made using well known methods such as spheronization or marumerization such that the bead core is highly drug loaded, or a sugar or other substance without any drug may be used as the starting core. Drug may be "buried" in the core or applied to any number of layers closer to the surface as desired. The method of applying overcoats of tabletting excipients can be applied to spheres which do not contain polymer coats. That is, drug containing spheres without polymer coats are often produced by marumerization and are useful for immediate release of drug but these spheres often do not form acceptable compacts (Schwartz et al.'s, *Compaction Studies on Beads: Compression and Consolidation Parameters, Drug Development and Industrial Pharmacy*, 20:3105–3129 (1994). Thus, the method presented herein of overcoating with a direct compression binder or a disintegrant or both is useful for compacting spheres for rapid disintegration and immediate and complete release of drug with no controlled release component. This may be particularly useful for highly potent drugs where uniform mixing of small amounts of drug with large amounts of powders is problematical but spray layering of accurately prepared solutions has fewer problems. This also is especially useful for large-dose drugs to maximize drug loading.

The polymer coating agents may be any known agents used as polymer coating films including those commonly used to sustain drug release from particulate dosage forms or as enteric coating agents. The hydrophilic gel forming agent may be applied before the polymer coat, after the polymer coat, on both sides of the polymer coat, or mixed in with the polymer coat, and may be any agent which gels sufficiently when exposed to an aqueous environment that the hydrophilic gel forming agent plays a role in controlling release of the active ingredient. The compact may be formulated and used in a manner where the compact disintegrates either relatively rapidly or relatively slowly so that disintegration occurs during use, or may be crushed prior to use. It will readily be recognized by those skilled in the art that each of these situations will require modifications in the formulation ingredients employed such as the types and amounts of hydrophilic gel forming agents, polymer coats, disintegrants, lubricants, flavors, etc. Methods and processes to optimize formulations using the basic concepts disclosed herein are well known.

While we have described and given examples of preferred embodiments of our inventions, it will be apparent to those of ordinary skill in the art that changes and modifications may be made without departing from our inventions in their broader aspects. We therefore intend the appended claims to cover all such changes and modifications as fall within the true spirit and scope of our invention.

We claim:

1. A chewable tablet made from drug delivery pellets, each drug delivery pellet comprising:
    a core portion comprising an active agent; and
    a coating for the core portion, the coating and core portion forming a discrete body, the coating comprising a hydrophilic gel-forming agent undercoating or mixed with a polymeric rate-controlling material.

2. A drug delivery pellet, comprising:
    a core portion comprising a therapeutic selected from the group consisting of proteins, polypeptides, and combinations thereof; and
    a coating for the core portion, the coating and core portion forming a discrete body, the coating comprising a hydrophilic gel-forming agent undercoating or mixed with a polymeric rate-controlling material.

3. A drug delivery pellet, comprising:
    a core portion comprising a diagnostic; and
    a coating for the core portion, the coating and core portion forming a discrete body, the coating comprising a hydrophilic gel-forming agent undercoating or mixed with a polymeric rate-controlling material.

4. A drug delivery pellet, comprising:
    a core portion comprising an active agent;
    a coating for the core portion, the coating and core portion forming a discrete body, the coating comprising a hydrophilic gel-forming agent undercoating or mixed with a polymeric rate-controlling material and an enteric coating.

5. A drug delivery pellet, comprising:
    a core portion comprising an active agent;
    a coating for the core portion, the coating and core portion forming a discrete body, the coating comprising a hydrophilic gel-forming agent undercoating or mixed with a polymeric rate-controlling material; and
    additional coatings applied over the coating for the core portion.

6. The pellets according to claim 5 wherein each pellet comprises plural hydrophilic gel-forming layers, and plural polymeric rate-controlling material layers.

7. A chewable tablet made by compacting plural self-sealing drug-delivery pellets, each pellet comprising:
    a core portion comprising an active agent selected from the group consisting of therapeutics, diagnostics and mixtures thereof; and
    a coating for the core portion, the coating and core portion forming a discrete body, the coating comprising a mixed layer of a hydrophilic gel-forming agent and a polymeric rate-controlling material.

8. Compactable, self-sealing drug-delivery pellets formulated for delivering a therapeutic to a lower portion of the gastrointestinal tract, each pellet comprising:
    a core portion comprising a therapeutic selected from the group consisting of proteins, polypeptides, and combinations thereof; and
    a coating for the core portion, the coating and core portion forming a discrete body, the coating comprising a mixed layer of a hydrophilic gel-forming agent and a polymeric rate-controlling material.

9. Compactable, self-sealing drug-delivery pellets, each pellet comprising:
    a core portion comprising an active agent selected from the group consisting of therapeutics, diagnostics and mixtures thereof;
    a coating for the core portion, the coating and core portion forming a discrete body, the coating comprising a mixed layer of a hydrophilic gel-forming agent and a polymeric rate-controlling material and an enteric coating.

10. A method for forming disintegrating tablets, comprising:
    forming an active agent delivery composition that includes a core portion comprising an active agent, and a coating for the core portion, the core portion and the coating forming a discrete body, the coating comprising a hydrophilic gel-forming agent undercoating or mixed with a polymeric rate controlling material and an enteric coating; and
    compressing a plurality of such bodies together to form a disintegrating tablet.

11. A method for forming disintegrating tablets, comprising:
    forming an active agent delivery composition that includes a core portion comprising a therapeutic selected from the group consisting of a protein, polypeptide, or combination thereof; and
    compressing a plurality of such bodies together to form a disintegrating tablet.

12. A method for forming disintegrating tablets, comprising:
    forming an active agent delivery composition that includes a core portion comprising an active agent, and a coating for the core portion, the core portion and the coating forming a discrete body, the coating comprising a hydrophilic gel-forming agent undercoating or mixed with a polymeric rate-controlling material, and an enzymatically or microbially degraded material that is useful for protecting the composition for site-specific delivery; and
    compressing a plurality of such bodies together to form a disintegrating tablet.

13. A method for forming disintegrating tablets, comprising:
    forming an active agent delivery composition that includes a core portion comprising an active agent, and a coating for the core portion, the core portion and the coating forming a discrete body, the coating comprising a hydrophilic gel-forming agent undercoating or mixed with a polymeric rate-controlling material and additional coatings; and
    compressing a plurality of such bodies together to form a disintegrating tablet.

14. A chewable tablet made from drug delivery pellets comprising a core portion comprising an active agent, and a coating for the core portion, the coating and core portion forming a discrete body, the coating comprising a hydrophilic gel-forming agent and a polymeric rate-controlling material.

15. A drug-delivery pellet, comprising:
    a core portion comprising a therapeutic selected from the group consisting of proteins, polypeptides, and combinations thereof; and
    a coating for the core portion, the coating and core portion forming a discrete body, the coating comprising a hydrophilic gel-forming agent and a polymeric rate-controlling material.

16. A drug-delivery pellet, comprising:
    a core portion comprising a diagnostic; and
    a coating for the core portion, the coating and core portion forming a discrete body, the coating comprising a hydrophilic gel-forming agent and a polymeric rate-controlling material.

17. A drug-delivery pellet, comprising:
    a core portion comprising an active agent;
    a coating for the core portion, the coating and core portion forming a discrete body, the coating comprising a hydrophilic gel-forming agent and a polymeric rate-controlling material; and
    an enteric coating over the polymeric rate-controlling material.

18. A drug-delivery pellet, comprising:
    a core portion comprising an active agent;
    a coating for the core portion, the coating and core portion forming a discrete body, the coating comprising a hydrophilic gel-forming agent, a polymeric rate-controlling material, and additional coatings.

19. A self-sealing, chewable tablet comprising plural compacted pellets, each pellet comprising:
    a core portion comprising an active agent selected from the group consisting of therapeutics, diagnostics and mixtures thereof; and
    a coating for the core portion, the coating and core portion forming a discrete body, the coating comprising a mixed layer of a hydrophilic gel-forming agent and a polymeric rate-controlling material.

20. Compactable, self-sealing, drug delivery pellets formulated for delivering active agents to a lower gastrointestinal tract, each pellet comprising:
    a core portion comprising an active agent comprising a therapeutic selected from the group consisting of proteins, polypeptides, and combinations thereof; and
    a coating for the core portion, the coating and core portion forming a discrete body, the coating comprising a mixed layer of a hydrophilic gel-forming agent and a polymeric rate-controlling material.

21. Compactable, self-sealing, drug delivery pellets, each pellet comprising:
    a core portion comprising an active agent selected from the group consisting of therapeutics, diagnostics and mixtures thereof;
    a coating for the core portion, the coating and core portion forming a discrete body, the coating comprising a mixed layer of a hydrophilic gel-forming agent and a polymeric rate-controlling material; and
    an enteric coating over the coating for the core portion.

22. Compactable self-sealing, drug delivery pellets, each pellet comprising:
    a core portion comprising an active agent selected from the group consisting of therapeutics, diagnostics and mixtures thereof; and
    a coating for the core portion, the coating and core portion forming a discrete body, the coating comprising a mixed layer of a hydrophilic gel-forming agent, a polymeric rate-controlling material, and additional coatings.

23. A method for forming disintegrating tablets, comprising:
    forming an active agent delivery composition that includes a core portion comprising an active agent, and a coating for the core portion, the core portion and coating forming a discrete body, the coating comprising a hydrophilic gel-forming agent, a polymeric rate-controlling material, and an enteric coating; and
    compressing a plurality of such bodies together to form a disintegrating tablet.

24. A method for forming disintegrating tablets, comprising:
    forming an active agent delivery composition that includes a core portion comprising a therapeutic agent selected from the group consisting of a protein, a polypeptide, or combinations thereof, and a coating for the core portion, the core portion and coating forming a discrete body, the coating comprising a hydrophilic gel-forming agent, and a polymeric rate-controlling material; and
    compressing a plurality of bodies together comprising the active agent delivery composition to form a disintegrating tablet.

25. A method for forming disintegrating tablets, comprising forming an active agent delivery composition that includes a core portion comprising an active agent, and a coating for the core portion, the core portion and coating forming a discrete body, the coating comprising a hydrophilic gel-forming agent that is an enzymatically or microbially degraded material that is useful for protecting the composition for site-specific delivery, and a polymeric rate-controlling material.

26. A method for forming disintegrating tablets, comprising:
    forming an active agent delivery composition that includes a core portion comprising an active agent, and a coating for the core portion, the core portion and coating forming a discrete body, the coating comprising a hydrophilic gel-forming agent, a polymeric rate-controlling material, and additional coatings; and
    compressing a plurality of bodies together comprising the active agent delivery composition to form a disintegrating tablet.

TABLE 3

| No. | compositions (at %) | mean crystal grain size D (μm) | thermal coefficient of Br (%/°C.) | magnetic properties | | |
|---|---|---|---|---|---|---|
| | | | | iHc (kOe) | Br (kG) | (BH) max (MGOe) |
| *1 | Fe-2B-15Nd | 6.0 | 0.14 | 1.0 | 9.6 | 4.0 |
| *2 | Fe-8B-15Nd | 5.5 | 0.14 | 9.5 | 12.3 | 33.2 |
| *3 | Fe-32B-15Nd | 10.1 | 0.16 | 11.0 | 2.5 | 1.3 |
| *4 | Fe-17B-30Nd | 7.3 | 0.16 | 14.8 | 4.5 | 4.2 |
| *5 | Fe-10Co-15B-5Pr | 22.0 | — | 0 | 0 | 0 |
| *6 | Fe-60Co-10B-13Nd | 15.7 | 0.07 | 0.6 | 7.9 | 2.8 |

TABLE 3-continued

| No. | compositions (at %) | mean crystal grain size D (μm) | thermal coefficient of Br (%/°C.) | magnetic properties | | |
|---|---|---|---|---|---|---|
| | | | | iHc (kOe) | Br (kG) | (BH) max (MGOe) |
| *7 | Fe-20Co-12B-14Pr | 110 | 0.09 | <1 | 5.7 | 1.8 |
| *8 | Fe-40Co-17B-15Nd | 0.85 | 0.07 | <1 | 6.1 | 1.4 |
| 9 | Fe-20Co-12B-14Pr | 8.8 | 0.09 | 6.8 | 10.4 | 19.5 |
| 10 | Fe-40Co-17B-15Nd | 2.8 | 0.06 | 6.5 | 9.2 | 17.1 |
| 11 | Fe-50Co-8B-15Nd | 4.7 | 0.06 | 1.5 | 8.7 | 5.5 |
| 12 | Fe-5Co-8B-15Nd | 29.0 | 0.11 | 6.4 | 11.3 | 25.2 |
| 13 | Fe-30Co-17B-15Nd | 36.5 | 0.08 | 5.2 | 8.6 | 13.6 |
| 14 | Fe-15Co-16B-16Pr | 68.0 | 0.09 | 3.6 | 10.2 | 9.4 |
| 15 | Fe-20Co-7B-15Nd | 5.6 | 0.09 | 8.6 | 12.1 | 31.9 |
| 16 | Fe-5Co-7B-15Nd | 6.5 | 0.11 | 9.0 | 12.5 | 34.2 |
| 17 | Fe-20Co-11B-7Pr | 17.5 | 0.09 | 6.3 | 9.5 | 14.7 |
| 18 | Fe-10Co-11B-7Nd-3Pr-5La | 22.3 | 0.10 | 4.8 | 7.7 | 9.8 |
| 19 | Fe-30Co-17B-22Nd | 13.5 | 0.08 | 4.4 | 5.4 | 4.8 |
| 20 | Fe-10Co-10B-5Ho-10Nd | 19.0 | 0.10 | 6.6 | 8.9 | 15.7 |
| 21 | Fe-10Co-10B-13Nd-2Dy-1La | 15.5 | 0.10 | 6.8 | 10.0 | 22.3 |
| 22 | Fe-20Co-9B-10Nd-6Pr-1Sm | 10.3 | 0.10 | 5.7 | 10.4 | 21.5 |
| 23 | Fe-15Co-7B-14Nd-2Gd | 7.5 | 0.10 | 4.7 | 9.7 | 16.7 |

TABLE 4 - 1

| No. | compositions (at %) | mean crystal grain size D (μm) | (BH) max (MGOe) |
|---|---|---|---|
| 1 | Fe-2Co-8B-15Nd-2Al | 4.8 | 29.5 |
| 2 | Fe-30Co-17B-13Nd-4Al | 7.4 | 17.6 |
| 3 | Fe-10Co-13B-14Nd-2Ti | 10.1 | 16.6 |
| 4 | Fe-10Co-13B-14Nd-2Ti | 75.0 | 4.3 |
| 5 | Fe-20Co-13B-16Nd-0.5Ti | 3.2 | 27.5 |
| 6 | Fe-35Co-8B-20Nd-1Ti | 25.0 | 11.2 |
| 7 | Fe-2Co-17B-16Nd-2V | 55.0 | 8.3 |
| 8 | Fe-20Co-12B-12Nd-0.5V | 5.2 | 21.5 |
| 9 | Fe-35Co-6B-20Nd-5V | 13.5 | 10.7 |
| 10 | Fe-5Co-7B-14Nd-3Cr | 8.7 | 16.0 |
| 11 | Fe-35Co-6B-23Nd-1Cr | 18.8 | 7.4 |
| 12 | Fe-15Co-16B-15Nd-1.5Mn | 21.2 | 14.6 |
| 13 | Fe-5Co-8B-17Nd-3Zr | 37.5 | 23.1 |
| 14 | Fe-10Co-20B-15Nd-0.5Hf | 28.0 | 12.6 |
| 15 | Fe-35Co-7B-20Nd-2Hf | 11.2 | 15.4 |
| 16 | Fe-3Co-8B-14Nd-1Nb | 5.0 | 36.0 |
| 17 | Fe-10Co-7B-17Nd-5Nb | 10.7 | 18.8 |
| 18 | Fe-5Co-15B-14Nd-1Ta | 16.2 | 11.4 |
| 19 | Fe-35Co-7B-15Nd-3Ta | 7.6 | 20.8 |
| 20 | Fe-2Co-8B-15Nd-0.5Mo | 6.5 | 33.5 |

* * * * *